United States Patent
Langereis et al.

(10) Patent No.: US 8,436,810 B2
(45) Date of Patent: May 7, 2013

(54) INDICATION OF THE CONDITION OF A USER

(75) Inventors: Geert Langereis, Eindhoven (NL); Evert Jan Van Loenen, Eindhoven (NL); Ralph Kurt, Eindhoven (NL); David Paul Walker, Redhill Surrey (GB); Steffen Reymann, Redhill (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 778 days.

(21) Appl. No.: 12/293,115

(22) PCT Filed: Mar. 7, 2007

(86) PCT No.: PCT/IB2007/050752
§ 371 (c)(1),
(2), (4) Date: Sep. 16, 2008

(87) PCT Pub. No.: WO2007/107900
PCT Pub. Date: Sep. 27, 2007

(65) Prior Publication Data
US 2009/0128487 A1    May 21, 2009

(30) Foreign Application Priority Data
Mar. 21, 2006  (EP) .................................. 06111475

(51) Int. Cl.
G09G 5/00  (2006.01)
(52) U.S. Cl.
USPC .............................. 345/156; 368/10; 600/300

(58) Field of Classification Search .................. 345/156; 600/300
See application file for complete search history.

(56) References Cited

U.S. PATENT DOCUMENTS

| | | | |
|---|---|---|---|
| 5,719,825 A * | 2/1998 | Dotter | 368/10 |
| 6,126,595 A * | 10/2000 | Amano et al. | 600/300 |
| 6,269,054 B1 | 7/2001 | Truini | |
| 6,304,519 B1 | 10/2001 | Druk | |
| 6,314,058 B1 * | 11/2001 | Lee | 368/10 |
| 2001/0049471 A1 * | 12/2001 | Suzuki et al. | 600/300 |

FOREIGN PATENT DOCUMENTS

| | | |
|---|---|---|
| DE | 7228348 U | 1/1973 |
| DE | 19531479 A1 | 2/1997 |
| DE | 202005001156 U1 | 6/2005 |
| EP | 0760224 A1 | 3/1997 |
| EP | 1575010 A1 | 9/2005 |

* cited by examiner

Primary Examiner — Viet Pham

(57) ABSTRACT

A wearable electronic device such as a wrist watch (60) is supplied with conventional clock with two pointers (32,33). The device displays a parameter indicative of how "cool" the wearer has been over the past period as a function of time, using the time axis of one of the pointers (32,33). "Coolness" can be based on the measurement of related physiological parameters like heart-rate, body temperature, movement, skin resistance or muscle activity. "Coolness" of a person is understood as being the ability to cope with stress. Therefore, the stability of physiological parameters can be used to derive a signal for the subjective trait called "coolness". All physiological parameters can be measured by sensors (10) in the watch (60) or in the strap (50). The invention is used as a gadget for self expression and emotional feedback.

10 Claims, 2 Drawing Sheets

INDICATION OF THE CONDITION OF A USER

BACKGROUND OF THE INVENTION

1. Technical Field

The present invention relates to an apparatus, system and method for indicating a user's condition.

2. Description of Related Art

Apparatuses for indicating the condition of a user are known. For example, in health clubs wrist watches are used by people during their work out for measuring and displaying a physiological parameter, such as heart rate.

Such a health watch is disclosed in the U.S. Pat. No. 6,314,058. It comprises sensors for measuring physiological parameters of its user. The watch comprises a window with a graphic in which the value of the heart rate of the user is displayed as a function of time. In this graph, the time axis is depicted along the X-axis and the value of the heart rate is depicted along the Y-axis. This consumes space on the front of the watch, which is limited.

It is an object of the invention to use less space for displaying the condition of the user of an apparatus.

SUMMARY OF THE INVENTION

According to an aspect of the invention an apparatus is provided for displaying time of the type using at least a rotatable pointer. The apparatus is also adapted for displaying the condition of a user. It comprises sensing means for sensing one or more physiological parameters of the user. It furthermore comprises display means being adapted for displaying the one or more sensed parameters or an indicator derived there from as a function of time, using the time axis of the rotatable pointer. In this way, a graph which is already present on the apparatus, namely the graph for indicating the time by a pointer is also used for displaying the condition of the user. Thereby, the limited space on the apparatus is used efficiently. Furthermore, the used time axis is very intuitive. At a single glance the user understands its scale.

The sensed physiological parameters of the user may be translated into a single "coolness" parameter. The "coolness" of an individual is understood as being the ability to cope with stress. For example, a person who does not alter his or her heart rate in a critical situation may claim he or she is cool. Therefore, the stability of physiological parameters can be used to derive a signal for the subjective term of trait called "coolness".

The apparatus according to the invention is used as a gadget for self expression and emotional feedback.

According to a first embodiment the display means are adapted for displaying the one or more sensed parameters or an indicator derived there from over a time period of 12 hours, i.e. using the time axis of the pointer used for indicating the hours. In this way, the user can easily see how his emotional condition was over the last 12 hours or in other words how "cool" he has been and thereby review his day. The use of the time axis of the pointer for indicating hours is very intuitive. For example, the value measured at 3 pm is plotted at 90 degrees, the value measured at 6 pm at 180 degrees, etc. The time axis can even be invisible (except of some markers 12-3-6-9) as it is known to the user to which time it corresponds.

Alternatively, the display means are adapted for displaying the one or more sensed parameters or an indicator derived there from over a time period of 1 hour i.e. using the time axis of the pointer used for indicating the minutes. This is often also very relevant to see. For example a user can show (to friends) his coolness in certain situations e.g. how relaxed he took it when he was criticized by his teacher or when asking a beautiful girl for a date etc. It is also possible to provide the apparatus with means for selecting a first mode in which the 12 hour time scale is used and a second mode in which the one hour scale is used.

In a preferred embodiment the apparatus comprises processing means for determining an average or normal value of one or more physiological parameters or the indicator derived there from for a user. Subsequently, the difference between the one or more physiological parameters or the indicator derived there from and the user's average or normal value is calculated by the processing means and finally displayed by the display means. In this way, the user and potentially persons in the user's environment can easily see the effect on his body by a potentially stressful event.

In a further preferred embodiment at least one of the connections between the sensing means, the processing means and the displaying means is by means of wireless RF, for example Bluetooth. This results in a modular structure of the apparatus, allowing the sensing means, processing means and display means to be present at a certain distance from each other without the need to use awkward wiring.

Alternatively, the processing means are not part of the apparatus but are part of a server. The sensing means and the display means are included in the apparatus. The apparatus comprises communication means for communicating with the server. The sensors and the display means are part of an apparatus. By placing the processing means in a server a different functionality is obtained. The user may adapt the algorithms used for processing and indicate his emotional condition by accessing the corresponding web page. It would be possible to charge a small fee to the user.

In a further preferred embodiment, the apparatus is a wearable electronic device. A concern for teenagers is that they are struggling with their role in the community. For people at this age it is important what others think of them and if they are still "cool". For this reason, for people in this age wearable electronic devices do not only serve a functional purpose, they are also used for self-expression. MP3 players, mobile phones and watches are used for their primary function, but their looks and features are used to compete with friends. This is especially done between teenagers and youngsters. The aim is to look cool and technologically up-to-date.

In a further preferred embodiment the wearable electronic device is a wrist watch. The sensors for measuring physiological parameters can be easily integrated into the watch itself or into its strap. Furthermore, according to this embodiment a typical self-expression piece of electronics, the wrist watch is equipped with the ability to give emotional feedback.

The invention gives feedback on the "coolness". It must be seen as a toy to play with and to share your personal training with others, mainly for fun.

Preferably, the invention is implemented by a computer program loaded into the processing means. In the preferred embodiment as a single watch with the sensors in the watch, this computer program runs in the internal software (firmware) of the watch.

These and other aspects of the invention will be apparent from and elucidated with reference to the embodiments described hereinafter.

BRIEF DESCRIPTION OF THE DRAWINGS

The invention will be better understood and its numerous objects and advantages will become more apparent to those skilled in the art by reference to the following drawing, in conjunction with the accompanying specification, in which.

Throughout the figures like reference numerals refer to like elements.

DETAILED DESCRIPTION OF THE PRESENT INVENTION

Figure 1:
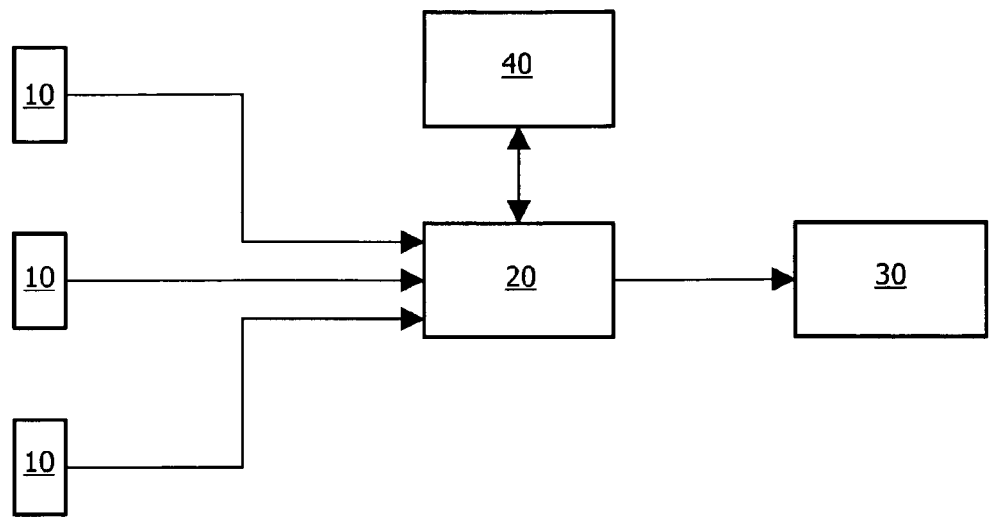
FIG. 1 shows a block diagram of a first embodiment of an apparatus for indicating the condition of a user.

With reference to FIG. 1 a block diagram of an apparatus for indicating the emotional condition of the user is described. The apparatus comprises one or more sensors 10 for measuring physiological parameters of its user. Most of these parameters can be measured on the wrist, by sensors in the watch. Therefore, in the preferred embodiment the whole system is integrated in a single wrist watch with the circular display as the intuitive ergonomic display.

Such parameters are for example:

Heart rate—to be measured by ECG electrodes on the wrist

Muscle contraction—measured by EMG electrodes on the wrist

Skin resistance—an indication of perspiration of the skin, easily measured with differential electrodes on the skin Skin temperature Movement—to be measured by an accelerometer Smell.

All these physiological parameters have a relation with the user's condition, for example a high heart rate implies stress, while minor variations in the skin resistance indicate coolness, etc. The sensors 10 are coupled by appropriate wiring to a processor 20. If the sensors are of the type having a digital output the coupling is direct, otherwise the coupling is through an A/D converter. The processor on its turn is coupled to a memory 40. The processor is also coupled to display means 30.

Figure 2:
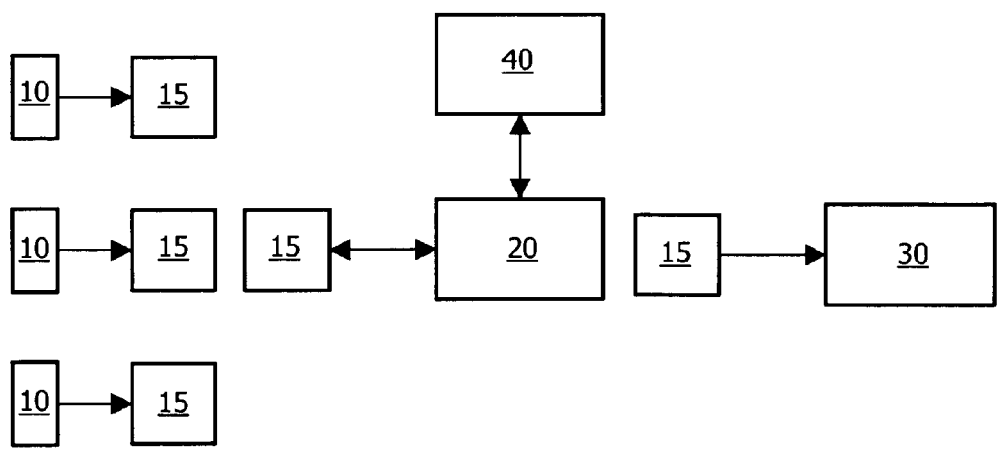
FIG. 2 shows a block diagram of a second embodiment of an apparatus for indicating the condition of a user.

In an alternative implementation the apparatus has a modular structure as shown in FIG. 2. The sensors 10, processor 20 and display means 30 are coupled to each other by means of wireless RF communication means 15, for example Bluetooth circuits. In a further alternative implementation only the sensors 10 and the processor 20 are coupled using wireless RF and the processor 20 and the display means 30 are in the same module.

The processor 20 is programmed with a suitable computer program for processing the data received by the sensors 10. Thereto, the measured parameters over this period are stored in the memory 40. The measured parameters are stored after certain time intervals, for example every minute. According to a first example the display means 30 simply display the value of one or more of the physiological parameters as a function of time over a period of 1 or 12 hours. Alternatively, the processor 20 calculates a single indicator derived from the physiological parameters as a function of time. According to a further alternative, the processor calculates an average or normal value for the one or more physiological parameters based on the measured parameters over a larger period of time, at least a few days. It then calculates the difference between the one or more physiological parameters and the user's average or normal value over a period of 1 or 12 hours. The display means 30 are adapted to display the difference as a function of time over a period of 1 or 12 hours. For displaying the difference (compared to a historical average) it is needed to predefine the scale, e.g. take the own historical min and max values ever measured. The current value most likely fits within this scale. One could also take the range of the highest and lowest value of yesterday (corresponding time period e.g. the same 12 hours) or of last week. The relative representation using the sensor readings with respect to an average is preferred because the abstract readout being "coolness" is the ability to maintain the normal body functions in stressful situations. With that in mind, the representation as the one could also use the first derivative of the body signals as "coolness" indicator, because it contains similar information. A first derivative of zero means maintenance of body signals, while an increase of the first derivative means stress.

The plurality of body signals can be reduced into a single "coolness" trend indicator by a weighted addition or multiplication of the sensor readings. For example, when both the heart rate and skin conductance is increasing, a person is apparently not resistive to conditions in his environment. It can be easier to interpret a single indicator than a whole series of body signals.

Long term viewing of measurement information can be done by transferring the data to a computer for example using USB or Bluetooth.

Figure 3:
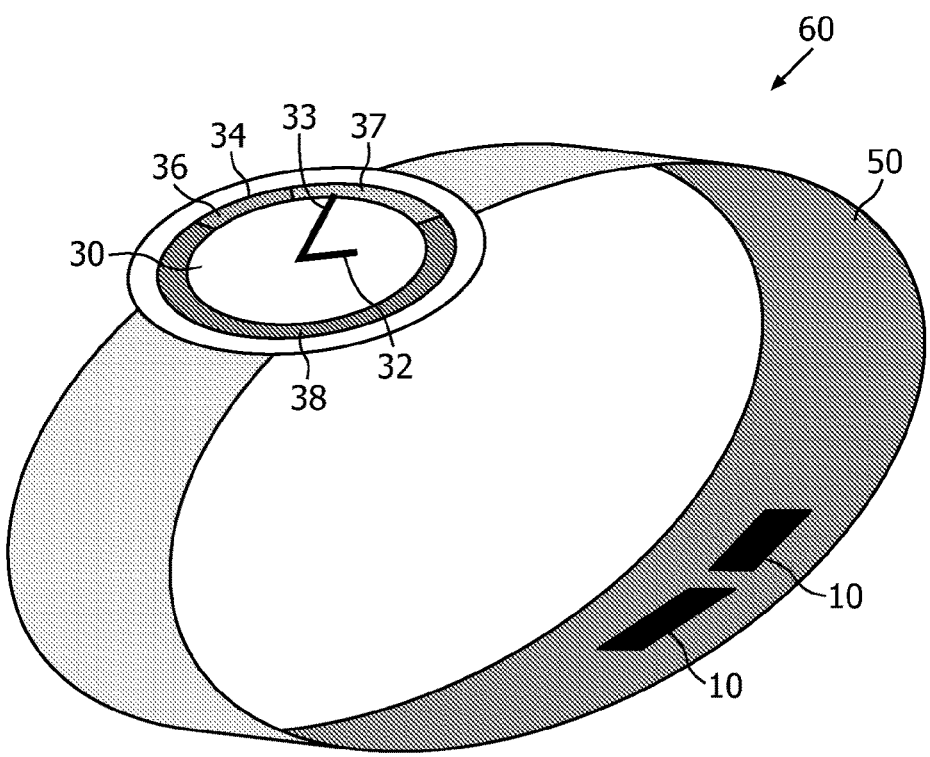
FIG. 3 shows an artist impression of a wrist watch for indicating the condition of a user in a first way.

In FIG. 3, an artist impression of a wrist watch 60 is shown. The sensors 10 are placed in the wrist strap (bracelet) 50, because on the inside of the arm the skin is the thinnest resulting in better signals. An alternative is to put them on the bottom of the clock module which reduces the problem of putting wires in the flexible strap or bracelet. It is very advantageous to place the sensors 10 in a wrist watch 60, because this is the most common piece of electronics worn on the naked skin. One of the sensors 10, or a combination of more than one, is used to give feedback to the person wearing the watch. The measurement data is displayed on the dial as shown in FIGS. 3, 4 and 5, because then the idea of the watch is optimally combined with the function of the emotional display.

The watch comprises a clock (radial display) having a dial, a first pointer 32 for indicating the hours and a second pointer 33 for indicating the minutes. So, the clock has two time axes: a first time axis corresponding to a period of 12 hours and a second time axis corresponding to a period of 60 minutes or 1 hour. The time axes may be indicated by a circle with some figures or they may be also invisible (except of some markers 12-3-6-9). Preferably, the outer circle 34 of the dial is used for displaying the condition of the user. The circle 34 represents the emotional condition of the user of the watch as a function of time for a period of 1 or 12 hours. A button may be provided on the watch for selecting a first mode in which the 12 hour time scale is used and a second mode in which the one hour scale is used.

Figure 4:
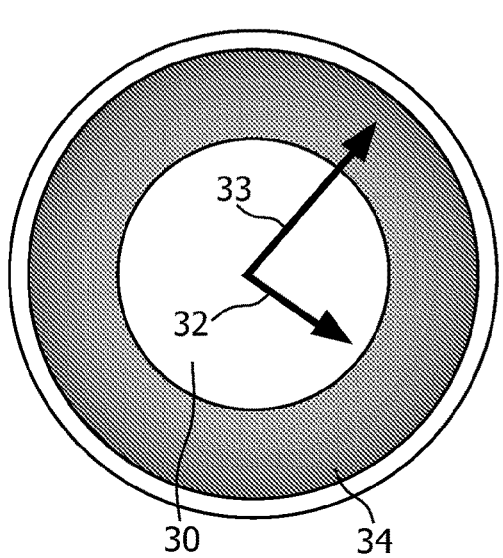
FIG. 4 shows the clock face of the wrist watch according to FIG. 3.
Figure 5:
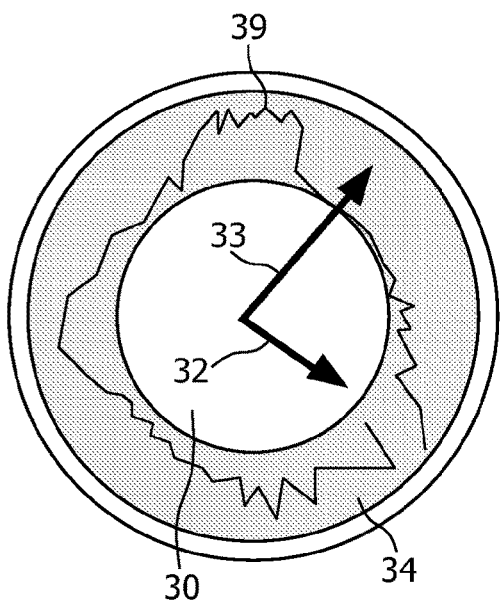
FIG. 5 the clock face of a wrist watch indicating the condition of a user in a second way.

In FIGS. 3-5 the watch has a circular shape but of course the invention may also be implemented in watches having other shapes, such as an elliptical, square, rectangular, triangular, hexagonal, octagonal or dodecagonal shape. In particular the hexagonal, octagonal or dodecagonal shape make it more intuitive to read out the emotional condition as function of time even if only a limited number of time indicators are used on the time axis.

According to a first example, the condition of the user is displayed for a 12 hour period using different colors. As shown in FIG. 3, three different parts of the circle 34 represent three different emotional conditions of the user. The current time is 16 h10. From approximately 11 h00 to 13 h00 hours the user was in a stressed condition, for example because due to an important meeting or an exam. This is indicated by showing the corresponding part 36 of the circle in red. From 13 h00-15 h00 the user was still a little stressed. This is indicated by showing the corresponding part 37 of the circle 34 in blue. During the rest of the 12 hour period, the user was relaxed or cool. This is indicated by showing the corresponding part 38 of the circle 34 in green.

Of course it is possible to use other colors for indicating the different emotional conditions of a user. Also more than three colors may be used, so that a larger amount of emotional conditions can be indicated.

Several ways of displaying are possible in the 12 hour mode:

According to a first alternative the last 12 hours of measured values are always shown. For example, if it is 15 h00, all values in the counter clockwise direction correspond to values measured recently. The values in the clockwise direction are values 12 hours old.

According to a second alternative each full circle of values is refreshed at 12 h00 noon and 24 h00 midnight. Again if it is 15 h00, the values counter clockwise are the recently measured values, whereas clockwise older reference values are displayed. These values are preferably the values of 24 hours ago, so to compare yesterday morning with this morning and comparing yesterday pm with today pm. One may also compare with older values, such as the pm values of 3 days ago, as this was also a challenging day. This comparison is often very interesting.

Alternatively, the user condition may be displayed as a graphic by using a line 39, running through the outer circle 34 as shown in FIG. 5. A value near the outer extreme of the circle for example represents a stressed condition, while a value near the inner extreme of the circle represents a cool or relaxed condition, or the other way around. The line 39 may be an indicator derived from a plurality of physiological parameters; Alternatively, the line 39 may directly represent the value of a single physiological parameter such as the user's heart rate. Alternatively, multiple physiological parameters may be represented, each by a single line in the graphic. According to a further alternative, the colors or the line 39 represent the user's condition compared to the user's average.

In case that there is a reference line in a first color (or in a first circular region) of the recent 12 hours and a second line of a second color as a reference showing the corresponding values of the same period 24 hours ago, the values of the present day may again be compared to older values.

Instead of a watch other "wearable" electronic devices may be used for providing feedback, such as a MP3-player of a mobile telephone. Both these devices have a display, on which a clock could be shown having two pointers for indicating the current time and an outer circle 34 for displaying the user's condition as discussed herein above.

According to a further example, the processing of the data measured by the sensor(s) may be done in a server (not shown). The communication to and from this server is carried out by means of a communication network, for example the internet. The sensors and display means are provided in an apparatus. The apparatus comprises suitable (wireless) communication means for sending the measured data to the server. The processing of the measured data in the server occurs in the same way as explained herein above for the processor. The server transmits the data to be displayed periodically or on request to the apparatus. The display means 30 are adapted for displaying the data received from the server as a function of time over a period of 1 or 12 hours. The user may adapt the algorithms used for processing and indicate his emotional condition by accessing the corresponding web page. It is possible to charge a small fee for this service.

Preferably, the apparatus enables a user to manually scroll back in the own history, for example by means of a button or the like. The historical values are always displayed at the corresponding place in the clock. For instance one could overlay or compare the current values with some older files, displaying next to each other or on top of each other, for example the values of 2 days ago or a week ago.

It is also possible to provide the apparatus with mobile communication means. This enables a user to share his/her data with friends by using SMS. Several plots may be displayed for example the current values or the last 12 hours (or last hour). In this way the user can show his/her friends how cool he is. This could become a competitive game: which user is the coolest in an exam period or other periods of stress, etc.

Preferably, there is a radial indicator indicating at which part of the circle the current new values are written. The pointer of the watch or an extended line from this pointer is suitable there for. This indicator has two functions, to pronounce the difference between the current value and the reference and to show if the display is in the 12 h or 1 h mode, linked to the short or the long pointer respectively. The pointers may have intuitive colors.

Of course the invention is also applicable for devices having rotating pointers with time axes unequal to 1 hour or 12 hours. For example, there are watches with a pointer that makes one rotation every 24 hours. In such a watch the condition of its user may be shown as a function of time using the time axis of this pointer, corresponding to a 24 hour period.

As will be recognized by those skilled in the art, the innovative concepts described in the present application can be modified and varied over a wide range of applications.

Accordingly, the scope of patented subject matter should not be limited to any of the specific exemplary teachings discussed, but is instead defined by the following claims.

Any reference signs in the claims shall not be construed as limiting the scope thereof.

The invention claimed is:

1. An apparatus for displaying time of a type using at least a rotatable pointer on a dial with a circular time axis, and further being adapted for indicating an emotional condition of a user thereof, the apparatus comprising:
   sensing means for sensing at least one physiological parameter of the user; and
   display means concurrently displaying (i) time and (ii) a single indicator representative of the emotional condition of the user derived from a stability of the at least one sensed physiological parameter as a function of time, wherein the time and the single indicator use the circular time axis of the rotatable pointer, and
   wherein displaying the single indicator includes displaying within an outer circle of the dial a current value and a plurality of past values of the single indicator for a predetermined period of time that is selectable between a first mode that uses a twelve hour time scale of the circular time axis and a second mode that uses a one hour time scale of the circular time axis.

2. The apparatus according to claim 1, wherein the predetermined period of time is 12 hours.

3. The apparatus according to claim 1, wherein the predetermined period of time is 1 hour.

4. The apparatus according to claim 1, wherein the apparatus comprises processing means adapted for determining a user's average or normal value for the single indicator derived from the stability of the at least one sensed physiological parameter and calculating a difference between a current value of the single indicator and the user's average or normal value and wherein the display means are further adapted for displaying the difference.

5. The apparatus according to claim 4, wherein at least one of the connections between the sensing means, the processing means and the display means is by means of wireless RF.

6. The apparatus according to claim 1, wherein the apparatus is incorporated in a wearable electronic device.

7. The apparatus according to claim 6 wherein the wearable electronic device is a wrist watch.

8. A system comprising an apparatus for displaying time of a type using at least a rotating pointer on a dial with a circular time axis, and further being adapted for indicating an emotional condition of a user thereof, the apparatus comprising:
   sensing means for sensing at least one physiological parameter of the user;
   display means being adapted for concurrently displaying (i) time and (ii) a single indicator representative of the emotional condition of the user derived from a stability of the at least one physiological parameter as a function of time, wherein the time and the single indicator use the circular time axis of the rotating pointer; and
   processing means for processing the at least one sensed physiological parameter, the processing means being part of a server, and wherein the apparatus further comprises communication means for communicating with the server,
   wherein displaying the single indicator includes displaying within an outer circle of the dial a current value and a plurality of as values of the single indicator for a predetermined period of time that is selectable between a first mode that uses a twelve hour time scale of the circular time axis and a second mode that uses a one hour time scale of the circular time axis.

9. A method comprising the following steps
   displaying time by an apparatus using at least a rotatable pointer on a dial with a circular time axis, and indicating an emotional condition of a user of the apparatus comprising the further steps of:
   sensing at least one physiological parameter of the user; and
   concurrently displaying (i) time and (ii) a single indicator representative of the emotional condition of the user derived from a stability of the at least one sensed physiological parameter as a function of time, wherein the time and the single indicator use the circular time axis of the rotatable pointer, and
   wherein the displaying the single indicator includes displaying within an outer circle of the dial a current value and a plurality of past values of the single indicator for a predetermined period of time that is selectable between a first mode that uses a twelve hour time scale of the circular time axis and a second mode that uses a one hour time scale of the circular time axis.

10. A computer program embodied on a non-transitory computer readable medium comprising computer program code means adapted to perform the following steps, when said program is run on a computer:
    processing sensed physiological parameters of a user; and
    concurrently displaying (i) a time and (ii) a single indicator representative of an emotional condition of the user derived from a stability of the at least one sensed physiological parameter as a function of time, wherein the time and the single indicator use a circular time axis of a rotatable pointer on a dial with the circular time axis used for displaying time, and
    wherein the displaying the single indicator includes displaying within an outer circle of the dial a current value and a plurality of past values of the single indicator for a predetermined period of time that is selectable between a first mode that uses a twelve hour time scale of the circular time axis and a second mode that uses a one hour time scale of the circular time axis.

\* \* \* \* \*